United States Patent [19]
Iannucci et al.

[11] Patent Number: 4,975,274
[45] Date of Patent: Dec. 4, 1990

[54] SODIUM GLUTAMATE AS AN ADDITIVE IN HAIR CARE PRODUCTS AND HAIR CARE PRODUCTS CONTAINING SAME

[75] Inventors: Joseph L. Iannucci, Milford; Jose E. Ramirez; Anthony L. Patti, both of Trumbull, all of Conn.

[73] Assignee: Chesebrough-Pond's USA Co., Division of Conopco, Inc., Greenwich, Conn.

[21] Appl. No.: 366,227

[22] Filed: Jun. 12, 1989

[51] Int. Cl.[5] .................. A61K 7/075; A61K 7/08
[52] U.S. Cl. .................... 424/70; 252/DIG. 13; 514/788
[58] Field of Search ............ 424/70, 71, 72; 252/DIG. 13; 514/561, 663, 667, 669, 784, 788, 880, 881, 574

[56] References Cited

U.S. PATENT DOCUMENTS 4,134,411  1/1979  Yamazaki ................... 424/71 X
4,412,943  11/1983 Hirota et al. .............. 252/DIG. 13
4,459,284  7/1984  Azuma et al. ............... 424/71 X
4,530,829  7/1985  Abe ........................ 424/70
4,542,014  9/1985  Bresak et al. .............. 424/70

FOREIGN PATENT DOCUMENTS 108704  8/1981  Japan ...................... 424/71
109711  7/1982  Japan ...................... 424/70

OTHER PUBLICATIONS

Shampoo Components-1985, Cosmetics & Toiletries, vol. 100, Mar. 1985, pp. 31-46.
R. S. Burnett, "Proteins in Cosmetics", American Perfumer and Cosmetics, vol. 78, No. 10, Oct. 1963, pp. 69-72.

Primary Examiner—Merrell C. Cashion, Jr.
Assistant Examiner—Susan S. Rucker
Attorney, Agent, or Firm—Milton L. Honig

[57] ABSTRACT

Hair care compositions are provided that include glutamic acid and water soluble salts thereof to improve the flexibility and elasticity of the treated hair.

5 Claims, No Drawings

SODIUM GLUTAMATE AS AN ADDITIVE IN HAIR CARE PRODUCTS AND HAIR CARE PRODUCTS CONTAINING SAME

This is a continuation-in-part application of Ser. No. 311,381, filed Feb. 16, 1989 which is a continuation application of Ser. No. 892,117 filed Aug. 4, 1986 both now abandoned.

This invention relates to the use of glutamic acid and water soluble salts thereof as an additive for water-containing hair care products so that the hair when treated with such products will have a desirable flexibility and resistance to breakage. The additive preferably used in accordance with this invention is monosodium glutamate, known in the art as MSG.

This invention also relates to hair care products containing glutamic acid and water soluble glutamate salts, preferably monosodium glutamate (MSG), in an effective amount to make the hair more flexible and more resistant to breakage when treated with such hair care products. Among the water-containing hair care products in which the incorporation of MSG has been found to improve the flexibility and resistance to breakage of the hair are shampoos, hair conditioner compositions, gel hair fixers, gel mousses, waving lotions and neutralizers.

BACKGROUND OF THE INVENTION

Prior work into proteins and the incorporation of proteins into hair products naturally lead us to the exploration of amino acids and their effects on hair. Experimentation with many amino acids showed that Lysine, Glutamic acid and monosodium glutamate (MSG) were capable of hydrating the hair. Cost considerations led us to develop the use of monosodium glutamate in hair care products.

The effects shown are that lysine, glutamic acid and MSG reduced the forces required to stretch the hair. This was verified by Instron Testing, which is a commonly used tool of hair research. The Instron machine is a very sophisticated strain gauge that can be used to stretch hair in a very precise and controlled manner and to determine quantitatively how much force was used to stretch and break the hair fiber. Using a split fiber technique it was found that when the same hair fiber was treated with a product that contained lysine, glutamic acid, or MSG, it required less force to stretch it than when it was treated with a product that contained none of these compounds. This is a surprising finding, since known hair moisturizing agents do not show this effect even when used in much greater amounts. When less force is required to stretch the hair it is generally interpreted to mean that the hair is moisturized (hydrated), thereby making it more flexible. This increased flexibility makes the hair more resistant to breakage during combing.

OBJECTS OF THE INVENTION

It is an objective of this invention to provide a method for improving the ability of water-containing hair care products to leave the hair in a desirable state of flexibility and a suitable elasticity.

A still further object of this invention is to provide at a reasonable cost an improved water-containing hair care composition capable of facilitating hydration of the hair so as to leave the hair with a desired flexibility and elasticity.

Yet a further object of this invention is to provide at a reasonable cost an improved water-containing hair shampoo composition which when applied to the hair facilitates hydration of the hair so as to increase the flexibility and elasticity of the hair leaving the hair softer, smoother, more resistant to breakage and more manageable (e.g., easier to comb) without detracting from the foaming and cleaning ability of the shampoo.

A still further object of this invention is to provide at a reasonable cost an improved water-containing hair shampoo composition which improves the luster, silkiness, body and resistance to breakage of the hair.

Yet another object of this invention is to provide at a reasonable cost an improved water-containing hair conditioner composition which may be applied to wet or dry hair and worked into the hair and left on the hair to provide desirable conditioning and manageability.

Another object of this invention is to provide at a reasonable cost an improved water-containing hair conditioner composition which when applied to the hair facilitates hydration of the hair to increase its flexibility and elasticity which makes the hair more resistant to breakage as well as being softer, smoother and easier to comb.

A still further object of this invention is to provide at a reasonable cost an improved water-containing hair conditioner composition which when applied to the hair imparts to the hair a better luster, more curl retention and better body.

Yet another object of this invention is to provide at a reasonable cost an improved water-containing hair pomade which when applied to the hair facilitates hydration of the hair to increase its flexibility and elasticity so that the hair is softer, smoother and easier to comb (manageability) with resultant reduction in hair breakage.

Another object of this invention is to provide improved water-containing gel fixers which when applied to the hair increases its flexibility and elasticity.

Another object of the invention is to provide an improved neutralizer which when applied to the hair increases its flexibility and elasticity.

GENERAL DESCRIPTION OF THE INVENTION

It has been found that the objects of this invention may be realized by incorporating in conventional hair care products (e.g., shampoos, hair conditioner compositions, hair pomades, gel hair fixers, gel mousses, waving lotions and neutralizers) an additive selected from the group consisting of glutamic acid and water soluble glutamic acid salts in an amount sufficient to facilitate hydration of the treated hair to a sufficient extent that there is a significant increase in the flexibility and elasticity (more resistant to breakage) of the hair.

The hydration effect observed with MSG is over and above conventional humectants, including water and seems to have a prolonged duration. While the invention is not limited to any theory of action effect may be MSG's ability to bind water on or in the hair fiber. This water may be already in the hair fiber and MSG may be helping to retain it or it may be water supplied by the product.

The additive preferably used in this invention is monosodium glutamate. Examples of other glutamate salts that may be used are potassium, ammonium and magnesium salts of glutamic acid. In addition to the additive, another essential component of the hair care products of this invention is water in an amount sufficient to solubilize an effective amount of the monosodium glutamate. the additive (e.g. monosodium glutamate) is in an amount 0.5 to 25%, preferably from about 0.5 to 5%, optimally between about 1.5 and about 3% by weight.

It has been found that the additive used in accordance with this invention is most effective in achieving the desired hydrating effect when the pH of the hair treating composition in the range of 4 to 11, and preferably 5 to 9.

The ability of the additive (e.g. MSG) to increase the flexibility and elasticity of the hair is achieved with various conventional hair care products. While the present invention is not based on any theory of action but rather the unexpected o ability of the additive (e.g. MSG) to improve the flexibility and elasticity of hair treated with hair care products containing the additive, it appears that the additive has the ability to facilitate hydration of the hair and such active hydration of the hair is believed to be responsible for the increase of the flexibility and elasticity of the hair.

For example, it has been found that when monosodium glutamate is incorporated in conventional hair shampoo in an expected amount (e.g. about 2% by weight), treatment with such shampoo facilitates hydration of the hair with an increase in flexibility and elasticity. This means that the shampooed hair was softer, smoother and easier to comb. The increased elasticity also made the hair more resistant to breakage. Advantageously, the normal ability of the shampoo to foam and clean was not affected.

The method of this invention may be carried out by incorporating sodium monoglutamate in conventional water-containing hair shampoo compositions. As is well known to those skilled in the art, conventional shampoos may contain the following components:

1. Carriers, preferably water, which acts as a solubilizer for all other ingredients and also as a moisturizing agent which helps hydrate the hair; the carrier will normally be present in an amount from about 30 to about 90, preferably between about 50 and 85%, optimally between about 50 and 65% by weight;
2. Detergents for cleaning the hair such, for example, as anionic detergents like the sodium, ammonium or triethanolammonium (TEA) salts of lauryl sulfate, alpha olefin sulfonate and lauryl ether sulfate; nonionic detergents; amphoteric detergents like cocoamidopropyl betaine and cocobetaine, and mixtures of the various detergents; the amounts of these detergents may range from about 1% up to about 50%, with the aninic types usually ranging from about 20 to 45% and the amphoteric types ranging from about 1 to 8%, preferably between 3 and 5% by weight;
3. Foaming agents and hair conditioners (such as TEA lauryl sulfate, lauramide DEA, cocamide DEA, acetamide MEA and mixtures thereof), the amount of these materials being present from about 0.5 to 10%, preferably from about 3% to 5% by weight;
4. Chelating agents to remove extraneous metallic ions found in water which may interfere with viscosity development (e.g., sodium EDTA); the amount of chelating agents will range from about 0.001 to about 1%, preferably between about 0.05 and 0.20% by weight; and,
5. Buffer or pH adjusting agents (e.g., citric acid) the amount of these agents in total ranging from about 0.05 to about 5%, preferably from about 0.1 to about 0.3% by weight.

It shall be understood that the specific types and grades of detergents that can be used will have an effect on the viscosity of the final composition. Thus, the desired thickness of the shampoo may affect what detergent and grade thereof would be preferred. In order to obtain thick shampoos if this be desired, the detergent used should have a grade with low sodium chloride content and low sulphate content. While one may prefer shampoos of different viscosities, it has been found that foaming, cleansing ability and the hydrating effect do not appear to change to any significant extent by varying the viscosity of the shampoo.

It has also been found that when an effective amount of monosodium glutamate (e.g. 2% by weight) is incorporated in a known hair conditioner composition, such composition may be effectively applied to wet or dry hair and worked into the hair and left on the hair to provide conditioning and manageability. Treatment with said hair conditioner composition facilitates hydration of the hair and imparts thereto increased flexibility and elasticity. The hair was softer, smoother and easier to comb, the increased elasticity making the hair more resistant to breakage. The treated hair had better luster, more curl retention and better body.

As is well known to those skilled in the art, hair conditioner compositions may contain the following components:

1. Carriers—preferably water to act as a solubilizer as well as a moisturizing agent; the carrier will normally be present in an amount from about 30 to about 90%, preferably between about 50 and 85%, optimally between about 50 and 65% by weight.
2. Lustering Agents—to impart shine or luster to the hair (e.g., mineral oil); the amount of such agents ranging from about 1 to about 10%, preferably between about 3 and about 8% by weight.
3. Body and Thickening Agents—to impart body to the hair and to serve as a stabilizer if an emulsion is present (e.g., Xanthan gum). The gum is used to stabilize the emulsion by creating a lattice structure in the water phase. For conditioners, gums used to stabilize the product must be chosen for their tolerance of salts. As an example, the salt resistant form of Veegum will yield a stable emulsion whereas its regular form will not. The amounts of such agents will range from about 0.1 to about 5%, preferably between about 0.2 and 1.5% by weight.
4. Waxy Agents—to impart hold and manageability to the hair such as Polawax; amounts of such agents will range from about 1 to about 10%, preferably from about 1.5 to about 5% by weight.
5. Emulsion Stabilizing Agents—non-ionic surfactants (e.g. sodium oleate, glycerol stearate, PEG 8 stearate, PEG 10 stearate, PEG 100 stearate, sorbitan oleate and ceteth-20); the amounts of such agents will range from about 0.1 to about 10%, preferably between about 0.5 and 5% by weight).
6. Buffer of pH adjusting agents—(e.g. citric acid the amount of these agents in total ranging from about 0.05 to about 5%, preferably from about 0.1 to about 0.3% by weight).

Also, it has been found that when an effective amount of monosodium glumate (e.g. 2% by weight) is incorporated in a known hair pomade composition, treatment with such a product facilitates hydration of the hair. The treated hair has increased flexibility and elasticity.

This means for the user that the hair will be softer, smoother and easier to comb which would result in reduced hair breakage.

As is well known to those skilled in the art, hair pomades may contain the following compounds.
1. Emollient or Lubricant—to coat hair shaft with thin layer, therefore holding hair in desired shape (e.g., petrolatum, mineral oil and wax modifiers).
2. Water—moisturizing agent
3. Surfactants—to solubilize aqueous phase into emollient or lubricant.
4. Coloring agent
5. Fragrance
6. Preservatives

SPECIFIC DESCRIPTION OF THE INVENTION

Example 1

This example relates to the preparation of a shampoo in accordance with the present invention A hair shampoo was made of the following formula:

FORMULA 1

| INGREDIENT | % BY WEIGHT |
| --- | --- |
| PHASE A | |
| Water, Deionized | 60.63000 |
| Disodium EDTA | 0.05000 |
| Sodium Lauryl Sulfate (Stepanol WA Paste) | 25.00000 |
| TEA-Lauryl Sulfate (MaproFix TLS 513 | 5.00000 |
| Lauramide DEA (Monamide 150 LM WC) | 4.75000 |
| Citric Acid | 0.27000 |
| Monosodium Glutamate | 2.00000 |
| Methylparaben NF | 0.15000 |
| Propylparaben NF | 0.10000 |
| PHASE B | |
| Water, Deionized | 1.24875 |
| Coloring Agents | 0.00135 |
| PHASE C | |
| DMDM Hydantoin (Glydant) | 0.30000 |
| Fragrance Agent | 0.50000 |
| | 100.00000% |

In Formula 1, the ingredients are added for the following reasons:

| Composition: | |
| --- | --- |
| Water | Moisturizing agent, helps hydrate hair and acts as solubilizer for all other ingredients. |
| Disodium EDTA | Chelating agent used to remove extraneous metallic ions found in water which may interfere with viscosity development. |
| Sodium Lauryl Sulfate | Active ingredient; detergent used to clean hair. |
| TEA Lauryl Sulfate Lauramide DEA | Active ingredients; enhance foaming and act as conditioners for hair. |
| Citric Acid | pH adjustment. |
| Monosodium Glutamate | Active ingredient used for conditioning and other properties. |
| Methylparaben, Propylparaben DMDM Hydantoin | Preservatives for system |
| Coloring Agent | To impart color. |
| Fragrance Agent | To impart fragrance. |

In making the hair shampoo of Example 1 from Formula 1, the following procedure is employed:
1. Charge a suitable vessel equipped with propeller mixer with water of Phase A. Begin heating to maximum temperature of 55° C. Also begin adding ingredients of Phase A in order of addition listed in formula. Do not add next ingredient until previous ingredient is fully dissolved. Avoid incorporation of air and adjust speed of mixing as product thickens with addition of MSG. When completed, begin cooling.
2. Retain some water of Phase B for rinsing vessel. Charge a suitable vessel with remainder of Phase B water and add dyes. Mix until fully dissolved and add to batch at 45° C.
3. At 35° C. add Phase C ingredients to batch. Submit batch for quality control analysis before filling.

In using the hair shampoo of Example 1 the hair should be wet thoroughly. Small amounts of the shampoo should then be applied to the hair. The hair should then be rubbed vigorously until a copious foam is formed. The hair should be rinsed thoroughly and the aforedescribed procedure be repeated. The resulting hair will be cleaned and shiny as well as being more flexible and easy to manage.

COMPARISON

A comparison was carried out to evaluate and compare two shampoos, one being the shampoo of Example 1 which contains monosodium glutamate and being referred to as "Shampoo A" and a second shampoo without monosodium glutamate and referred to as "Shampoo B".

The shampoo comparison experiment may be described as follows:

PANEL PROFILE: Eleven black female panelists with chemically treated hair.

METHOD: Standard blind half-head shampoo comparison done weekly for five consecutive weeks. No other hair aids (conditioner, pomade, curl activator, etc) were applied during the test study.

The following results were obtained.

On initial and first week shampoos there appeared to be no dramatic difference in any categories. However, on the third week, shampoo "A", scored higher than shampoo "B" in the following categories: feel of hair, manageability, and gives body. At the fourth week, shampoo "A" continually scored higher than "B" in (initial lather) speed and durability, (second lather) volume, (dry evaluation) luster, feel of hair and manageability. At the fifth week shampoo, there was a slight difference in speed of shampoo and volume of shampoo "A" was better in these two categories. There was no difference between the shampoos on wet and dry combing.

Example 2

This example relates to a preparation of a hair shampoo in accordance with the present invention.

A hair shampoo was made of the following formula:

| INGREDIENT | % BY WEIGHT |
| --- | --- |
| PHASE A | |
| Water deionized | 51.89000 |
| Disodium EDTA | 0.05000 |
| Sodium Alpha-Olefin ($C_{14}$–$C_{16}$ Sulfonate (Siponate A246L Low Salt: [Alcolac Co.]) | 25.00000 |
| TEA-Lauryl Sulfate (Maprofix TLX-513) | 5.00000 |
| Lauramide DEA (monamide 150 LM WC) | 4.75000 |
| Acetamide MEA | 3.75000 |

-continued

| INGREDIENT | % BY WEIGHT |
|---|---|
| Coco-Betaine (Velvetex AB-45) | 5.00000 |
| PHASE B | |
| Citric Acid | 0.26000 maximum |
| Methylparaben NF | 0.15000 |
| Propylparaben NF | 0.10000 |
| Monosodium Glutamate | 2.00000 |
| PHASE C | |
| Water | 1.24875 |
| Coloring Agents | 0.00125 |
| PHASE D | |
| DMDM Hydantoin (Glydant) | 0.30000 |
| Fragrance Agent | 0.5000 |
| | 100.00% |

In formula 2 the ingredients are added for the following reasons:

| Composition: | |
|---|---|
| Water | Moisturizing agent, helps hydrate hair and acts as solubilizer for all other ingredients. |
| Disodium EDTA | Chelating agent used to remove extraneous metallic ions found in water which may inhibit viscosity development. |
| Sodium Alpha Olefin ($C_{14}$–$C_{16}$) Sulfonate | Active ingredient, main detergent used to clean hair; removes grime and excessive oil. |
| TEA-Lauryl Sulfate Lauramide DEA Acetamide MEA Coco-Betaine | Active ingredients; conditions hair; aid in wet and dry combing and enhance foaming and detergency, reduced tangles, increases manageability, reduces static charge and stabilizes foam. |
| Citric Acid | pH adjustment. |
| Monosodium Glutamate | Active ingredient; hydrates hair. |
| Methylparaben Propylparaben DMDM Hydantoin | Preservative system. |
| Coloring Agents | To impart color. |
| Fragrance Agents | To impart fragrance. |

In making the hair shampoo of Example 2 from Formula 2, the following procedure is employed:
1. Charge a suitable vessel equipped with a propeller mixer with water of Phase A. Begin heating to a maximum temperature of 65° C. Also begin adding ingredients of Phase A in order of as they appear in the formula. Monamide 150LM WC must be premelted and mixed; also, Velvetex AB-45 should be prewarmed and mixed.
2. When a clear, homogenous solution forms, begin adding Phase B ingredients in order listed. Do not add next ingredient until previous ingredient is completely dissolved. Add Citric Acid starting with 0.15% and add until pH of 6.5±0.1 is reached.
3. When completed, begin cooling and add Phase C ingredients.
4. At 35° C. add Phase D ingredients. Submit a batch to Q.C. for analysis before filling.

The hair shampoo of Example 2 is used in the same manner as the hair shampoo of Example 1. It cleans the hair and imparts body, luster and silkiness to the hair.

Example 3

This example relates to the preparation of a hair conditioner composition in accordance with the present invention.

A hair conditioner composition was made of the following formula:

| FORMULA 3 | |
|---|---|
| INGREDIENT | % BY WEIGHT |
| PHASE A | |
| Water, Deionized | 83.775 |
| Magnesium Aluminum Silicate (Veegum HS) | 0.800 |
| Xanthan Gum (Keltrol M) | 0.200 |
| Citric Acid | 0.075 |
| Methylparaben NF | 0.150 |
| PHASE B | |
| Polawax | 3.000 |
| Mineral Oil, 70 SUS | 5.000 |
| Ceteth-20 (Brij 58) | 2.500 |
| Sorbitan Oleate (Span 80) | 2.000 |
| Propylparaben NF | 0.100 |
| PHASE C | |
| Monosodium Glutamate | 2.000 |
| PHASE D | |
| DMDM Hydantoin (Glydant) | 0.200 |
| Fragrance Agent | 0.2000 |
| | 100.000% |

In Formula 3 the ingredients are added for the following reasons:

| Composition: | |
|---|---|
| Water | Moisturizing Agent, helps to hydrate hair and acts as solubilizer for Monosodium Glutamate. |
| Magnesium Aluminum Sulfate | Active ingredients. |
| Xanthan Gum | Naturally occurring thickener used to stabilize emulsion and to impart body to hair. |
| Citric Acid | pH adjustment. |
| Polawax | Active ingredient. Self emulsifying was used to impart hold and manageability to hair. |
| Mineral Oil | Active ingredient. To impart shine or luster to hair |
| Ceteth-20 Sorbitan Oleate | Non-ionic surfactants used to stabilize emulsion system. |
| Monosodium Glutamate | Active ingredient used for conditioning; |
| Propylparaben Methylparaben DMDM Hydantoin | Preservatives for system. |
| Fragrance Agent | To impart fragrance. |

In making the hair conditioner from the above Formula 3 the following procedure is employed:
1. Charge a suitable vessel, equipped with a high speed propeller with Phase A water. Using the highest possible speed carefully disperse Veegum HS to fully hydrate (approximately one hour). Carefully disperse the Keltrol M in the same manner. When fully dispersed begin heating to 75° C. At 65° C. add the citric acid and the methylparaben.
2. Separately heat and mix Phase B to 75° C.
3. Add Phase B to Phase A at 75° C. Provide adequate mixing and avoid air entrapment. Cool to 65° C.
4. At 65° C. add Phase C, Monosodium Glutamate, to batch. Mix and cool.
5. At 35° C. add Phase D to batch. Mix and cool. Submit sample for Q.C. analysis before filling.

6. When QC approval is received the batch can be filled at 20° C.-30° C. The hair conditioner/curl activator composition of Example B is a leave-on conditioner that imparts luster, body and manageability to the hair.

In using the composition of Example 2 a small amount is applied to clean wet or dry hair after which the composition is rubbed through the hair with a vigorous motion. The hair is then combed into the desired shape. The composition may be reapplied as often as necessary.

The above referred to application of Example 2 to hair actively conditions the hair; improves luster and manageability while leaving the hair silky feeling. It also adds to the hair curl retention and gives body to the hair.

COMPARISON

A comparison was carried out to evaluate and compare two hair conditioner compositions, one being the composition of Example 2 which contains monosodium glutamate and being referred to as "Hair Conditioner Composition A" and a second hair conditioner composition free of monosodium glutamate and referred to as "Hair Conditioner Composition B."

The hair conditioner comparison experiment may be described as follows: PANEL PROFILE: Eleven black female panelists with chemically treated hair. METHOD: Standard blind half-head conditioner comparison done weekly for five (5) consecutive weeks. No other hair aids (pomades, hair spay, etc.) were applied during the test study.

The following results were obtained.

On initial and first week conditioner and rechecks there appeared to be virtually no difference in the conditioners. At the recheck of the third conditioner, hair conditioner "A", scored better than "B" in curl retention and feel of hair A and B. At the fourth week conditioner and recheck there was a slight difference in luster; at both times "A" was better. At the last conditioner test, "A" was better than "B" in the following categories: dry combing, luster, and bounce.

Example 4

This example relates to a hair conditioner composition in accordance with this invention.

A hair conditioner composition was made of the following formula:

| FORMULA 4 | |
|---|---|
| INGREDIENT | % BY WEIGHT |
| PHASE A | |
| Water Deionized | 82.175 |
| Sequestrene, Disodium | 0.050 |
| Citric Acid | 0.175 |
| Monosodium Glutamate | 2.000 |
| Methylparaben NF | 0.150 |
| PHASE B | |
| Dicetyldiamonium Chloride (Adogen 432CG - Sherex) | 2.000 |
| Cetyl Alcohol NF | 4.000 |
| Polawax | 4.000 |
| Stearamidopropyl Dimethylamine (Lexamine S-13 - Inolex) | 0.500 |
| PEG-8 Stearate (Pegosperse 400 MS - Glyco) | 0.500 |
| Glyceryl Stearate & PEG 100 Stearate (Arlacel 165 - ICI) | 4.000 |
| Propylparaben NF | 0.100 |
| PHASE C | |

| FORMULA 4 | |
|---|---|
| INGREDIENT | % BY WEIGHT |
| DMDM Hydantoin (Glydant - Glyco) | 0.100 |
| Fragrance Agent | 0.250 |
| | 100.000% |

In Formula 4 the ingredients are added for the following reasons:

| Composition: | |
|---|---|
| Water | Moisturizing agent, helps to hydrate hair and act as solubilizer for MSG. |
| Sequestrene | Chelating agent to remove any extraneous metallic ions remaining in deionized water. |
| Monosodium Glutamate | Active ingredient used for conditioning [see previous data in Hair Conditioning, IHC-18-198A]. |
| Dicetyldiamonium Choride | Active ingredient; Conditioner that imparts body, luster and combability to hair through ionic attraction. |
| Cetyl Alcohol | Thickener and emulsion stabilizer. |
| Polawax | Active ingredient; imparts luster and body to hair; also emulsion stabilizer |
| Stearamidopropyl Dimethylamine | Active ingredient; conditions and imparts antistatic properties to hair. |
| PEG-8 Stearate Arlacel 165 | Solubilizers and emulsion stabilizers. |
| Citric Acid | To adjust pH. |
| Methylparaben Propylparaben DMDM Hydantoin | Preservation system |
| Fragrance Agent | To impart odor. |

In making the hair conditioner of Formula 4 the following procedure is followed:

1. Charge a suitable vessel with water, begin heating to 75° C. Add items in Phase A in order. Do not add next item until previous item in completely dissolved.
2. Separately heat and mix items in Phase B to 75° C. until fully dissolved.
3. When both phases are 75° C. and clear, slowly add Phase B to Phase A, with moderate agitation.
4. At 35° C. add Phase C and q.s. to weighed with water.
5. At 30° C. fill into containers. The hair conditioner of Example 4 is used in the same manner as the hair conditioner of Example 3.

Example 5

This example relates to the preparation of a hair pomade in accordance with the present invention.

A hair pomade was made of the following formula;

| FORMULA 5 | |
|---|---|
| INGREDIENT | % BY WEIGHT |
| PHASE A | |
| Petrolatum CP Color 2.5 Soft | 82.4000 |
| Mineral Oil White Grade 70 SUS | 6.7972 |
| Syncrowax HR-C (Glyceryl Tribehenate) | 3.0000 |
| Propylpharaben NF | 0.1000 |
| PHASE B | |
| Water, Deionized | 2.0000 |
| Monosodium Glutamate | 2.0000 |
| Methylparaben NF | 0.2000 |
| Polyaldo DGDO K FG | 3.0000 |

-continued

FORMULA 5

| INGREDIENT | % BY WEIGHT |
|---|---|
| (Decaglyceryl Decaoleate) | |
| PHASE C | |
| Coloring Agent | 0.0028 |
| PHASE D | |
| Glydant 40-700 | 0.3000 |
| (DMDM Hydantoin | |
| Fragrance Agent | 0.2000 |
| | 100.000 |

In the above Formula 5 the ingredients were added for the following reasons:

| Composition | |
|---|---|
| Petrolatum | Active ingredient. Emollient, lubricant, coats hair shafts with a thin layer, therefore holding hair in desired shape. |
| Mineral Oil | Emollient, lubricant, used to modify texture of petrolatum. |
| Syncrowax HR-C (Glyceryl Tribehenate) | Microcrystalline wax used to modify texture of petrolatum and give proper consistency. |
| Propyl and Methylparaben and Glydant (DMDM Hydantoin) | Preservatives for system. |
| Water | Moisturizing agent, helps hydrate hair. |
| Monosodium Glutamate | Active ingredient used for conditioning and other properties. [See accompanying memo.] |
| Polyaldo DGDO K FH (Decaglyceryl Decaoleate) | Surfactant used to solubilize aqueous phase into petrolatum. |
| Coloring Agent | To impart color. |
| Fragrance Agent | To impart fragrance. |

In making the hair pomade of this invention from Formula 3 the following procedure is employed:

1. In a suitable vessel, heat and melt together all of the ingredients of Phase A.
2. In a separate vessel equipped with a Lightnin Mixer, begin the preparation of Phase B by first heating the water to 75° C. Next add monosodium glutamate and dissolve fully. Maintaining the temperature at 75° C., and with high speed mixing, add methylparaben and, when fully dissolved, add Polyaldo DGDO Mix until uniform.
3. Add Phase B to Phase A with highest possible mixing rate. CAUTION; Both phases must be 75° C., avoid splattering and air entrapment. Mix until uniform and add Phase C. Begin cooling.
4. At 40° C. add fragrance and Glydant 40-700.
5. Fill into containers at 35° C. When the hair pomade of this invention is applied to the hair, it sets the hair and imparts to it a shiny appearance. It also improves the flexibility and elasticity of the hair whereby it is easier to manage. In use, a small amount of the product is applied to the fingers and rubbed thoroughly through the hair.

COMPARISON

A study was carried out to determine the effects of monosodium glutamate (MSG) in a hair pomade.

The hair pomade of Example 5 A containing monosodium glutamate ("Hair Pomade A") was compared with the identical composition except it contains no monosodium glutamate ("Hair Pomade B").

In the comparison test referred to below the hairs tested were Instron tested. An Instron is a very sophisticated strain gauge that can apply specific quantities of stress on a fiber. It takes a single hair fiber and stretches it until it breaks. By knowing how much force it took to stretch the hair one can tell how strong or how flexible the hair was originally. Hair is a very complex structure with fibrils intertwined within fibrils all in a matrix. When one stretches hair just a little one begins to uncoil these fibrils and, as more force is applied, one eventually breaks these structures. Each phase of this uncoiling has a characteristic pattern and when one graphs the stress vs. the strain applied to the hair one gets a characteristic curve. The first part of this curve is called the Hookean region and it is the area where one sees the most cosmetic effects of MSG. If the slope of this curve is less than that of the control it means that the hair took less force to uncoil it. Hence it was more flexible or more moisturized. When one compares the slope of the curves of the shampoo base with and without MSG one finds that it took less force to uncoil the hair when MSG was present. The same is true for the pomade, not only our base but when compared to a competitive product. Also true of our shampoo, when compared to competition. Also true of the conditioner, when compared to itself with and without MSG.

Thus, a composition such as those of the present invention which decreases the slope of the-Hookean region-as compared to untreated hair may be said to facilitate hydration of the hair. On the other hand, when a composition increases the slope of the hair as can occur with some prior art compositions containing no MSG this means that the composition has a drying effect on the hair. For further understanding of the significance of the change of the slope of the Hookean region one may review the article Chapter 8 of the publication Chemical and Physical Behavior of Human Hair by Clerence R. Robbins.

In the comparison test, Negroid hair, both virgin and straightened, and Caucasian hair, both virgin and twice bleached, were Instron tested. The tests were conducted at 20% RH on untreated hair sample; hair treated with pomade with MSG ("Hair Pomade A") and hair treated with pomade without MSG ("Hair Pomade B"). The following observations were made:

In all the cases, the MSG containing "Hair Pomade A" showed increased moisturization when compared to the "Hair Pomade B" containing no MSG:

| % Decrease in Hookean Region | |
|---|---|
| Negroid virgin hair | 15.0 |
| Negroid straightened hair | 11.5 |
| Caucasian virgin hair | 15.0 |
| Caucasion twice bleached hair | 8.7 |

The raw data Hookean region comparison between a hair pomade composition with and without MSG is shown in Table I.

TABLE I

RESULTS OF INSTRON TESTING

| | Hookean Region (gm/cm)* |
|---|---|
| Black Virgin Hair | |
| No MSG | 342.9 ± 20.5 |

TABLE I-continued
RESULTS OF INSTRON TESTING
Hookean

| | Region (gm/cm)* |
|---|---|
| With MSG | 291.0 ± 25.8 |
| Straightened Black Hair | |
| No MSG | 337.6 ± 16.5 |
| With MSG | 298.7 ± 15.0 |
| Virgin Brown Caucasian Hair | |
| No MSG | 413.5 ± 22.5 |
| With MSG | 351.3 ± 19.3 |
| 2× Bleached Caucasian Hair | |
| No MSG | 448.9 + 31.9 |
| With MSG | 409.2 ± 34.0 |

*Mean ±95% confidence limits

Example 6

This example relates to the preparation of a gel hair fixed in accordance with this invention.

A gel hair fixer was made of the following formula:

| FORMULA 6 | |
|---|---|
| INGREDIENT | % BY WEIGHT |
| PHASE A | |
| Water Deionized | 57.5046 |
| Carbopol 940 | 1.5000 |
| FD&C Blue #1 | 0.0004 |
| PHASE B | |
| Water, Deionized | 15.0000 |
| Sodium Hydroxide | 0.7200 |
| Propylpharaben NF | 0.1250 |
| Methylparaben NF | 0.1000 |
| PHASE C | |
| Water, Deionized | 16.000 |
| PVP K-30, GAF | 0.5000 |
| Glycerine | 5.0000 |
| Methyl Gluceth-20 | 1.0000 |
| Trisodium EDTA | 0.0100 |
| Fragrance | 0.2400 |
| Monosodium Glutamate | 2.0000 |
| DMDM Hydantoin | 0.3000 |
| | 100.0000% |

In Formula 6 the ingredients were added for the following reasons:

| | |
|---|---|
| Water: | Moisturing agent, helps to hydrate hair and act as solublizer for MSG. |
| Carbopol 940 | Gelling agent. |
| Sodium Hydroxide | Neurtralizing agent for Carbopol. |
| PVP-K30, GAF | Resin used to impart hold and set the hair.. |
| Glycerine- Methyl Gluceth-20 | Humectant used to impart shine to hair. |
| Monosodium Glutamate: | Active ingredient used for conditioning. |
| Propylpharaben Methylparaben Dmdm Hydantoin | Preservative system |
| Trisodium EDTA: | Chelating agent to remove any extranous metallic ions remaining in deionized water |

The procedure that was used to produce the gel hair fixer of Formula 5 is as follows:
1. In a suitable vessel and with high shear stirring, disperse Carbopol in water of Phase A. When fully dispersed begin heating to 75° C. and add dye.
2. In a separate vessel begin heating water of Phase C to 75° C. Add Trisodium EDTA. Disperse PVP K-30. Add Glycerine, Methyl Gluceth-20 and Monosodium Glutamate.
3. Premix and dissolve ingredients of Phase B, heating to 75° C.
4. When both vessels are at 75°, add Phase C to Phase A. Then Phase B to Phase A. Begin cooling to 35° C.
5. At 35° C., add fragrance and DMDM Hydantoin.

Example 7

This example relates to the preparation of a gel mousse in accordance with this invention.

A gel mousse was made of the following formula;

| FORMULA 7 | |
|---|---|
| INGREDIENT | % BY WEIGHT |
| PHASE A | |
| Water Deionized | 77.2996 |
| Disodium EDTA | 0.500 |
| Glycerine | 5.0000 |
| Carbopol 941 | 0.5000 |
| Hydroxyl Ethyl Cellulose | 0.5000 |
| Polysulfonic Acid | 2.0000 |
| FD&C Blue #1 | 0.004 |
| Methylparaben NF | 0.1500 |
| Propylparaben | 0.1000 |
| Monosodium Glutamate | 2.0000 |
| Ceteareth-20 | 1.0000 |
| Ammonium Hydroxide (58% Solution) | 0.6000 (max) |
| PHASE B | |
| Water, Deionized | 10.0000 |
| Fragrance | 0.0500 |
| DMDM Hydantoin | 0.3000 |
| | 100.0000% |

In Formula 7 the ingredients were added for the following reasons:

| | |
|---|---|
| Water: | Moisturizing agent, helps to hydrate hair and act as solubilizer for MSG. |
| Disodium EDTA: | Chelating agent to remove any extraneous metallic ions remaining in deionized water. |
| Glycerine | Humectant used to impart shine to hair. |
| Carbobol 941: | Gelling agent. |
| Hydroxy Ethyl Cellulose Polysulfonic Acid | Active ingredient. Resins used to impart set and hold to hair |
| FD&C Blue #1 | To impart color to product. |
| Methylparaben Propylparaben DMDM Hydantoin | Preservative system. |
| Monosodium Glutamate: | Active ingredient used for conditioning. |
| Ceteareth-20 | Used to condition hair. |
| Ammonium Hydroxide: | To adjust pH and neutralize carbopol. |
| Fragrance: | To impart odor to product. |

The procedure that was used to produce the gel mousse is as follows:
1. In a suitable vessel dissolve Disodium EDTA. Add Glycerine. With high speed stirring add Carbopol and Hydroxethyl Cellulose and begin heating to 75° C.
2. At 75° C. add color, Methylparaben, Polyparaben, Ceteareth-20, Polysulfonic Acid and Monosodium Glutamate.
3. Add Ammonium Hydroxide titrating to pH 6.5.

4. At 35° C. add fragrance, DMDM Hydantoin and remaining water.

| Aerosolize: Using piston or bag-in-can type container: | | |
|---|---|---|
| Internal fill: | Concentrate | 90.0% |
| | N-Pentane/Isobutane 90/10 | 10.0% |
| | | 100.0% |

Example 8

This example relates to the preparation of a hair waving composition.

The hair waving composition of this invention has the following formula:

| FORMULA 8 | |
|---|---|
| INGREDIENT | % BY WEIGHT |
| Amm. thioglycolate (60/5) Argus | 10.00 |
| Lanogel 41 | 0.50 |
| Hamp-Ex. 80 | 0.20 |
| Monoethanolamine QS to pH 9.25 | 2.41 |
| Latex E-308 | 0.50 |
| Brij 35 | 1.25 |
| Perfume RTP-4 | 0.50 |
| Deionized Water | 83.64 |
| Sodium Monoglutamate | 1.00 |
| | 100.00% |

The composition of Formula 8 has a pH of 9.33, a [thio] content of 5.95 and an [alk] of 3.31 cc/gms.

In Formula 8 the ingredients are added for the following reasons:

| FORMULA 8 | |
|---|---|
| Ammonium thioglycolate: | Active ingredient provides curls to the hair. |
| Lanogel 41: | Conditioning agent. |
| Hamp-Ex-80: | Chelating agent to remove extraneous metallic ions that would otherwise interfere with the waving lotion. |
| Monoethanolamine: | To adjust pH and also provide free alkalinity so permanent wave can react in a reasonable length of time. |
| Latex E-308: | Opacifying agent to give the product a lotion look. |
| Fragrance: | To impart a pleasant odor. |
| Deionized Water: | Vehicle for product, provides moisture for the hair and is a solubilizer for MSG. |
| Monosodium Glutamate: | Active ingredient used for conditioning. |
| Brij 35: | Wetting agent and solubilizer for perfume. |

The hair waving composition of Example 8 is made by the following procedure:

PROCEDURE

In making the permanent wave from example 8, formula 8, the following procedure should be employed:
1. Charge a suitable vessel equipped with a propeller mixer with about 97% of water.
2. Add Hamp-Ex 80 to batch container, stir until dissolved.
3. Add ammonium thioglycolate to batch, mix for 10 min.
4. Add monosodium glutamate to batch, stir until dissolved.
5. In separate vessel which can be heated mix Lanogel 41 with 1% of water, warm to dissolve, then add to batch. Rinse container with 1% of water.
6. In a separate vessel which can be heated melt Brij 35 (do not exceed 45° C.). Add perfume, mix until uniform. Add to batch. Rinse container with 1% of water.
7. Add monoethanolamine to batch, mix well for 10 min.
8. Add Latex E-308 to batch, mix well for 10 min.
9. Check batch for proper specification.

Example 9

This example relates to the preparation of a neutralizer composition used in the waving of hair.

The neutralizer composition of this invention has the following formula:

| FORMULA 9 | |
|---|---|
| INGREDIENT | % BY WEIGHT |
| Deionized water (High Resistance) | 95.1518 |
| Monosodium glutamate | 1.0000 |
| Hydrogen Peroxide (Albone 35 CG) | 3.7142 |
| Acetophenetin | 0.0500 |
| Phosphoric Acid (85%) | 0.0840 |
| | 100.0000% |

In formula 9 the ingredients are added for the following reasons:

| Deionized Water: | Vehicle for product, provides moisture for the hair and is a solubilizer for MSG. |
|---|---|
| Monosodium Glutamate: | Active ingredient used for conditioning. |
| Albone 35 CG (Hydrogen Peroxide) | Active ingredient, used to neutralize reducing agent left on the hair in the waving process. |
| Phosphoric Acid (85%): | To adjust pH to proper level. |
| Acetophenetin: | Acts as as stabilizer for hydrogen peroxide. |

The neutralizer of Formula 9 is made by the following procedure:

PROCEDURE FOR FORMULA 9

NOTE: All equipment must be properly passivated and only very high resistance water is to be used.
1. In a separate heated jacketed kettle, equipped with a propeller mixer, add 15% of water; heat to 180° F. (82° C.). Add acetophenetin, stir until dissolved.
2. In batch mixing tank, equipped with a propeller mixer, add remaining water, then add monosodium glutamate, stir until dissolved.
3. To batch mixing tank, add the acetophenetin-water mixture. Stir will for 20 min.
4. Add hydrogen peroxide (Albone CG) to batch mixing tank, stir for 10 min.
5. Add phosphoric acid to batch, mix well for 10 min.

Example 10

This Example illustrates a further series of shampoos according to the present invention.

|  | Shampoo Formula No. (Hair Type) | | | |
|---|---|---|---|---|
| Ingredient | Formula 10A (Normal) | Formula 10B (Normal) | Formula 10C (Oily) | Formula 10D (Regular) |
| Water | 53.70 | 64.70 | 62.70 | 64.70 |
| Sodium Lauryl 2 EO Sulfate | 38.00 | — | — | — |
| Sodium Lauryl 3 EO Sulfate | — | 15.00 | 16.00 | 14.00 |
| TEA Lauryl Sulfate | — | 10.00 | 11.00 | 11.00 |
| Cocodiethanolamide | 3.00 | 3.00 | 3.00 | 3.00 |
| Cocoamidopropyl betaine | 1.75 | 4.00 | 4.00 | 4.00 |
| Disodium EDTA | 0.05 | 0.05 | 0.05 | 0.05 |
| Methylparaben | 0.15 | 0.15 | 0.15 | 0.15 |
| Propylparaben | 0.10 | 0.10 | 0.10 | 0.10 |
| Citric Acid | 0.25 | 0.10 | 0.10 | 0.10 |
| Colorant | 0.065 | 0.065 | 0.065 | 0.065 |
| DMDM Hydantoin (Glydant 40-700) | 0.30 | 0.30 | 0.30 | 0.30 |
| Perfume | 0.50 | 0.50 | 0.50 | 0.50 |
| Monosodium Glutamate | 2.00 | 2.00 | 2.00 | 2.00 |
| Sodium chloride | 0.17 | — | — | — |
| Glycerine | — | — | — | 0.05 |

Example 11

This Example illustrates a typical hair conditioner.

| Ingredient | Weight % |
|---|---|
| Water | 87.62 |
| PEG-100 Stearate | 3.00 |
| Monosodium Glutamate | 2.00 |
| Dicetyldimonium Chloride | 2.00 |
| Cetyl Alcohol | 1.75 |
| Emulsifying Wax | 1.75 |
| PEG-8 Stearate | 0.50 |
| Stearamidopropyl Dimethylamine | 0.50 |
| Perfume | 0.20 |
| Citric Acid | 0.175 |
| DMDM Hydantoin (Glydant 40-700) | 0.15 |
| Methylparaben | 0.15 |
| Propylparaben | 0.10 |
| Disodium EDTA | 0.05 |

What is claimed is:

1. An improved hair care composition consisting of:

| Water | 53.70% |
|---|---|
| Sodium Lauryl 2 EO Sulfate | 38.00% |
| Cocodiethanolamide | 3.00% |
| Cocoamidopropyl betaine | 1.75% |
| Disodium EDTA | 0.05% |
| Methylparaben | 0.15% |
| Propylparaben | 0.10% |
| Citric Acid | 0.25% |
| Colorant | 0.065% |
| DMDM Hydantoin | 0.30% |
| Perfume | 0.50% |
| Monosodium Glutamate | 2.00% |
| Sodium chloride | 0.17% |

2. An improved hair care composition consisting of:

| Water | 64.70% |
|---|---|
| Sodium Lauryl 3 EO Sulphate | 15.00% |
| TEA Lauryl Sulfate | 10.00% |
| Cocodiethanolamide | 3.00% |
| Cocoamidopropyl betaine | 4.00% |
| Disodium EDTA | 0.05% |
| Methylparaben | 0.15% |
| Propylparaben | 0.10% |
| Citric Acid | 0.10% |
| Colorant | 0.065% |
| DMDM Hydantoin | 0.30% |
| Perfume | 0.50% |
| Monosodium Glutamate | 2.00% |

3. An improved hair care composition consisting of:

| Water | 62.70% |
|---|---|
| Sodium Lauryl 3 EO Sulfate | 16.00% |
| TEA Lauryl Sulfate | 11.00% |
| Cocodiethanolamide | 3.00% |
| Cocoamidopropyl betaine | 4.00% |
| Disodium EDTA | 0.05% |
| Methylparaben | 0.15% |
| Propylparaben | 0.10% |
| Citric Acid | 0.10% |
| Colorant | 0.065% |
| DMDM Hydantoin | 0.30% |
| Perfume | 0.50% |
| Monosodium Glutamate | 2.00% |

4. An improved hair care composition consisting of:

| Water | 64.70% |
|---|---|
| Sodium Lauryl 3 EO Sulfate | 14.00% |
| TEA Lauryl Sulfate | 11.00% |
| Cocodiethanolamide | 3.00% |
| Cocoamidopropyl betaine | 4.00% |
| Disodium EDTA | 0.05% |
| Methylparaben | 0.15% |
| Propylparaben | 0.10% |
| Citric Acid | 0.10% |
| Colorant | 0.065% |
| DMDM Hydantoin | 0.30% |
| Perfume | 0.50% |
| Monosodium Glutamate | 2.00% |
| Glycerine | 0.05% |

5. An improved hair care composition consisting of:

| Water | 87.62% |
|---|---|
| PEG-100 Stearate | 3.00% |
| Monosodium Glutamate | 2.00% |
| Dicetyldimonium Chloride | 2.00 |
| Cetyl Alcohol | 1.75% |
| Emulsifying Wax | 1.75% |
| PEG-8 Stearate | 0.50% |
| Stearamidopropyl Dimethylamine | 0.50% |
| Perfume | 0.20% |
| Citric Acid | 0.175% |
| DMDM Hydantoin | 0.15% |
| Methylparaben | 0.15% |
| Propylparaben | 0.10% |
| Disodium EDTA | 0.05% |

* * * * *